US010427998B2

(12) United States Patent
Pigamo et al.

(10) Patent No.: US 10,427,998 B2
(45) Date of Patent: Oct. 1, 2019

(54) COMPOSITIONS BASED ON 1,1,3,3-TETRACHLOROPROPENE

(71) Applicant: ARKEMA FRANCE, Colombes (FR)

(72) Inventors: Anne Pigamo, Francheville (FR); Bertrand Collier, Saint-Genis-Laval (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/575,980

(22) PCT Filed: May 4, 2016

(86) PCT No.: PCT/FR2016/005105
§ 371 (c)(1),
(2) Date: Nov. 21, 2017

(87) PCT Pub. No.: WO2016/189214
PCT Pub. Date: Dec. 1, 2016

(65) Prior Publication Data
US 2018/0148394 A1 May 31, 2018

(30) Foreign Application Priority Data
May 22, 2015 (FR) ...................... 15 54655

(51) Int. Cl.
C07C 17/25 (2006.01)
C07C 17/20 (2006.01)
C07C 21/04 (2006.01)
C07C 17/266 (2006.01)
C07C 17/269 (2006.01)
C07C 17/087 (2006.01)
C07C 19/01 (2006.01)
C07C 19/08 (2006.01)
C07C 21/18 (2006.01)
C07C 17/38 (2006.01)
C07C 17/093 (2006.01)
C07C 17/383 (2006.01)
C09K 5/04 (2006.01)

(52) U.S. Cl.
CPC .......... C07C 17/206 (2013.01); C07C 17/093 (2013.01); C07C 17/25 (2013.01); C07C 17/266 (2013.01); C07C 17/269 (2013.01); C07C 17/383 (2013.01); C09K 5/044 (2013.01); C09K 5/045 (2013.01); C09K 2205/126 (2013.01); C09K 2205/24 (2013.01)

(58) Field of Classification Search
CPC .................................................. C07C 21/04
See application file for complete search history.

(56) References Cited

U.S. PATENT DOCUMENTS 5,616,819 A 4/1997 Boyce et al.
5,684,219 A 11/1997 Boyce

| | | | |
|---|---|---|---|
| 5,705,779 A | 1/1998 | Demmin et al. | |
| 5,877,359 A * | 3/1999 | Elsheikh | C07C 17/00 570/160 |
| 6,166,274 A | 12/2000 | Chen et al. | |
| 6,403,847 B1 * | 6/2002 | Nakada | C07C 17/00 570/153 |
| 8,404,907 B2 | 3/2013 | Nair et al. | |
| 8,426,656 B2 | 4/2013 | Merkel et al. | |
| 8,436,217 B2 | 5/2013 | Wang et al. | |
| 8,704,017 B2 | 4/2014 | Pokrovski et al. | |
| 8,877,990 B2 * | 11/2014 | Fukuju | C01B 7/01 570/226 |
| 9,255,045 B2 | 2/2016 | Pigamo et al. | |
| 9,834,499 B2 | 12/2017 | Pigamo et al. | |
| 10,077,221 B2 | 9/2018 | Bonnet et al. | |
| 2010/0191025 A1 | 7/2010 | Perdrieux | |
| 2011/0196178 A1* | 8/2011 | Nyberg | C07C 1/26 570/160 |
| 2011/0197602 A1 | 8/2011 | Abbas et al. | |
| 2011/0201853 A1 | 8/2011 | Tung et al. | |
| 2011/0218370 A1 | 9/2011 | Elsheikh et al. | |
| 2011/0245549 A1 | 10/2011 | Merkel et al. | |
| 2012/0059199 A1 | 3/2012 | Pokrovski et al. | |
| 2012/0172636 A1* | 7/2012 | Pokrovski | C07C 17/206 570/135 |
| 2012/0190902 A1 | 7/2012 | Nyberg | |
| 2012/0226081 A1 | 9/2012 | Elsheikh et al. | |
| 2012/0271070 A1 | 10/2012 | Wang et al. | |
| 2012/0329893 A1 | 12/2012 | Abbas | |
| 2013/0037058 A1 | 2/2013 | Abbas | |
| 2013/0211154 A1 | 8/2013 | Cottrell et al. | |
| 2013/0261354 A1 | 10/2013 | Merkel | |
| 2014/0213831 A1 | 7/2014 | Nyberg | |
| 2014/0221704 A1 | 8/2014 | Tung et al. | |
| 2014/0264173 A1* | 9/2014 | Merkel | C07C 21/04 252/364 |
| 2015/0152235 A1 | 6/2015 | Abbas | |
| 2015/0197467 A1 | 7/2015 | Pigamo et al. | |
| 2016/0023974 A1 | 1/2016 | Bonnet et al. | |

(Continued)

FOREIGN PATENT DOCUMENTS

EP 0 940 382 A1 9/1999
FR 2768727 A1 3/1999

(Continued)

OTHER PUBLICATIONS

International Search Report (PCT/ISA/210) dated Jul. 13, 2016, by the European Patent Office as the International Searching Authority for International Application No. PCT/FR2016/051054.

(Continued)

Primary Examiner — Medhanit W Bahta
(74) Attorney, Agent, or Firm — Buchanan Ingersoll & Rooney P.C.

(57) ABSTRACT

The present invention relates to compositions based on F-1230za (1,1,3,3-tetrachloropropene), or on a mixture consisting of F-1230za and F-1230zd (1,3,3,3-tetrachloropropene), the manufacture thereof, and also the use thereof in particular for the production of F-1233zdE (trans-1-chloro-3,3,3-trifluoropropene), F-1234zeE (trans-1,3,3,3-tetrafluoropropene), and/or F-245fa (1,1,1,3,3-pentafluoropropane).

15 Claims, No Drawings

(56) References Cited

U.S. PATENT DOCUMENTS

| | | |
|---|---|---|
| 2016/0115104 A1 | 4/2016 | Pigamo et al. |
| 2017/0081263 A1 | 3/2017 | Klausmeyer et al. |
| 2018/0093934 A1 | 4/2018 | Pigamo et al. |
| 2018/0354875 A1 | 12/2018 | Bonnet |
| 2019/0048241 A1 | 2/2019 | Abbas et al. |

FOREIGN PATENT DOCUMENTS

| | | |
|---|---|---|
| WO | WO 2008/149011 A2 | 12/2008 |
| WO | WO 2008/149011 A3 | 12/2008 |
| WO | WO 2010/059496 A1 | 5/2010 |
| WO | WO 2010/111067 A1 | 9/2010 |
| WO | WO 2015/175791 A1 | 11/2015 |

OTHER PUBLICATIONS

Written Opinion (PCT/ISA/237) dated Jul. 13, 2016, by the European Patent Office as the International Searching Authority for International Application No. PCT/FR2016/051054.

Abbas, Laurent, et al., U.S. Appl. No. 16/027,743 entitled "Heat Transfer Method," filed Jul. 5, 2018.

Bonnet, Philippe, et al., U.S. Appl. No. 16/102,320 entitled "Composition Comprising HF and E-3,3,3-Trifluoro-1-Chloropropene," filed Aug. 13, 2018.

Rached, Wissam, U.S. Appl. No. 16/333,003 entitled "Composition Comprising 1-Chloro-3,3,3-Trifluoropropene," filed Mar. 13, 2019.

\* cited by examiner

COMPOSITIONS BASED ON 1,1,3,3-TETRACHLOROPROPENE

FIELD OF THE INVENTION

The present invention relates to compositions based on F-1230za (1,1,3,3-tetrachloropropene), or a mixture consisting of F-1230za and F-1230zd (1,3,3,3-tetrachloropropene), to the manufacture thereof, and also to the use thereof especially for the production of F-1233zdE (trans-1-chloro-3,3,3-trifluoropropene), F-1234zeE (trans-1,3,3,3-tetrafluoropropene) and/or F-245fa (1,1,1,3,3-pentafluoropropane).

TECHNICAL BACKGROUND

Fluoroolefins, and in particular F-1233zdE, are compounds of major interest for refrigeration and air-conditioning systems, given the new environmental regulations.

It is known practice to produce hydrofluoroolefins such as F-1233zdE by fluorination of hydrochloroolefins or chlorohydrocarbons in particular. This fluorination is generally a fluorination using hydrofluoric acid as fluorinating agent.

Among the routes for obtaining F-1233zdE, it is in particular known practice to use F-240fa (1,1,1,3,3-pentachloropropane) as starting compound. Reference is made, for example, to U.S. Pat. No. 8,704,017 in this regard, which describes a process of liquid-phase fluorination in the absence of catalyst but requiring several reactors in series and/or stirring of the reaction medium to counter the low degree of conversion.

US 2014/0 221 704 teaches the low miscibility between F-240fa and hydrogen fluoride, and proposes the addition of a phase-transfer agent to the reaction medium to solve this problem.

US 2013/0 211 154 suggests increasing the pressure in the reaction medium to improve the degree of conversion of F-240fa.

Another possible process is the liquid-phase fluorination of F-1230za, in the absence of catalyst and under much less severe conditions, this olefinic starting material not having these difficulties of low degree of conversion.

However, it is known that a liquid-phase fluorination process may generate several undesired compounds such as oligomeric compounds, products of high boiling point, toxic or corrosive compounds, or, more generally, impurities that are difficult to separate out. In particular, these oligomeric compounds have the consequence of reducing the efficiency of the fluorination process and must be separated out by a purge, in a continuous system or in a batch system, obtained from the reactor and retreated. Compounds of high boiling point may also prevent the reaction.

The harmful effects of impurities on fluorination processes were also observed in the abovementioned reaction of F-1230za.

Stabilization of tetrachloropropenes with inhibitors, generally antioxidants, is taught in US 2012/0 226 081, US 2012/0 190 902 or US 2014/0 213 831. These inhibitors prevent the formation of oxygenated impurities, mainly phosgene which is toxic, during the phases of transportation and storage. However, the impact of these impurities in a liquid-phase fluorination process is not described.

It is desirable to be able to produce F-1233zdE under good yield conditions on an industrial scale using a process that is simple to perform, especially in the liquid phase and in the absence of catalyst, which allows an improvement in the yield and/or which does not present any difficulties in terms of separating out undesired compounds.

SUMMARY OF THE INVENTION

The invention is based on the surprising discovery that when the starting material does not contain any specific impurities, or contains only very little thereof, the fluorination in the absence of catalyst of F-1230za, or of F-1230za mixed with F-1230zd, is markedly more efficient. The product stream is richer in F-1233zdE and contains fewer undesired compounds.

The invention relates firstly to a composition comprising at least 99.5% by weight of 1,1,3,3-tetrachloropropene or a mixture of 1,1,3,3-tetrachloropropene and of 1,3,3,3-tetrachloropropene, and comprising at least one compound chosen from a list of additional compounds consisting of pentachloropropanes (especially F-240fa), tetrachloropropenes other than F-1230za and F-1230zd (especially 1,1,2,3-tetrachloroprene (F-1230xa), chlorobutenes, chlorobutanes and oxygenated compounds (for example acids, esters, aldehydes or oxychlorides), said compound or the total amount of said compounds being present in the composition in a weight content of less than or equal to 0.5%.

In one embodiment, said additional compound is present in the composition in a weight content of less than or equal to 1000 ppm and the total amount of said compounds is less than or equal to 0.5%.

According to one embodiment, the composition comprises at least 99.5% by weight, preferably at least 99.7% by weight and particularly preferably at least 99.8% by weight of F-1230za, or of a mixture of F-1230za and of F-1230zd.

Secondly, the invention relates to a process for obtaining the composition as defined above.

Next, the invention relates generally to the use of said composition in the preparation of F-1233zd, and provides a particular process for producing 1-chloro-3,3,3-trifluoropropene, especially in trans form, comprising:
the provision of a composition as defined above;
the reaction of this composition with hydrofluoric acid.
Use may also be made of F-1230zd or else a mixture constituted of F-1230za and of F-1230zd as starting reagent.

According to the preferred embodiment, the process comprises a single fluorination step in the liquid phase and in the absence of catalyst.

In the course of the fluorination reaction(s), some of the impurities of the F-1230za may be converted into different impurities in the liquid reaction medium worked under standard temperature and pressure conditions and may accumulate in the reactor. These oligomers are harmful to the reactivity since they occupy the volume of the reactor and deteriorate the reaction yield. They may also be constituted of compounds which have a certain toxicity, or corrosiveness, which entails difficulties during their handling for destruction. They must thus be removed by means of a purge system before being treated and the final residue removed.

The present invention makes it possible to overcome the drawbacks of the prior art. The invention more particularly provides compositions based on F-1230za of which the content of specific impurities is controlled, making it possible to minimize the generation of harmful oligomers in the reaction medium of the process for manufacturing F-1233zdE.

DESCRIPTION OF EMBODIMENTS OF THE INVENTION

The invention is now described in greater detail and in a nonlimiting manner in the description which follows.

All the contents indicated are weight contents, unless otherwise mentioned.

Compositions According to the Invention

The invention proposes compositions based on F-1230za or a mixture of F-1230za and F-1230zd. The content of F-1230za or the sum of the contents of F-1230za and F-1230zd is greater than or equal to 99.5%.

According to certain embodiments, it is greater than or equal to 99.6%, or 99.7%, or 99.8%, or 99.9%, or 99.95%.

The compositions according to the invention also comprise at least one compound chosen from a list of additional compounds constituted by pentachloropropanes (especially 1,1,1,3,3-pentachloropropane or F-240fa), tetrachloropropenes (especially 1,1,2,3-tetrachloropropene or F-1230xa), chlorobutenes, chlorobutanes and oxygenated compounds, said compound being present in the composition in a content of less than or equal to 0.5% by weight; or less than or equal to 1000 ppm; or less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

The term "oxygenated compound" refers to any compound containing an oxygen heteroatom, such as acids, esters, aldehydes or oxychlorides, for instance phosgene.

Particularly undesirable impurities mixed in the reaction medium are:
 molecules of the F-240 series, such as F-240fa (1,1,1,3,3-pentachloropropane), F-240da (1,1,2,3,3-pentachloropropane), F-240db (1,1,1,2,3-pentachloropropane), F-240ab (1,1,1,2,2-pentachloropropane), and more particularly F-240db and F-240fa;
 molecules of the F-1230 series, other than F-1230za and F-1230zd, such as F-1230xa (1,1,2,3-tetrachloropropene), F-1230xd (1,2,3,3-tetrachloropropene), F-1230xf (2,3,3,3-tetrachloropropene), and more particularly the abovementioned F-1230xa;

The molecules F-240fa, F-240db and F-1230xa are chlorinated impurities which have undesired behavior in the reaction medium in the presence of HF and in the absence of catalyst. F-240fa has a low degree of conversion and has a certain stability in the reaction medium. It may lead to sparingly fluorinated compounds such as F-241fa (1,1,3,3-tetrachloro-1-fluoropropane) with a high boiling point. They have a tendency to encumber the volume of the reaction medium without reacting sufficiently. The case is substantially the same for F-240db. On the other hand, the molecule F-1230xa generates a large amount of oligomers when it is heated in the presence of HF and in the absence of catalyst.

Consequently, it is desirable to adjust the compositions according to the invention so as to limit the presence of these chlorinated impurities.

Thus, advantageous compositions according to the invention:
 comprise at least one compound from among those of the F-240 series in a content of less than or equal to 0.5%; or less than or equal to 1000 ppm; or less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and, for example, from 1 to 5 ppm; and/or
 comprise at least one compound from among those of the F-1230 series, other than F-1230za and F-1230zd, in a content of less than or equal to 0.5%; or less than or equal to 1000 ppm; or less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and, for example, from 1 to 5 ppm; or alternatively
 comprise at least one compound from among F-1230xa, F-240fa and F-240db, in a content of less than or equal to 0.5%; or less than or equal to 1000 ppm; or less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and, for example, from 1 to 5 ppm.

Other particularly undesirable impurities mixed in the reaction medium are also chlorinated molecules containing four carbon atoms. These high-boiling compounds also accumulate in the reactor, encumber the reaction volume and may lead, to a lesser extent, by fluorination and rearrangement of the molecule to a four-carbon fluorinated compound whose high toxicity is well known, namely perfluoroisobutylene (PFIB).

These impurities contained in the starting material are thus:
 molecules of the type such as chlorobutanes, dichlorobutanes, trichlorobutanes and in particular the tetrachlorobutane family such as 1,1,4,4-tetrachlorobutane, 1,2,3,4-tetrachlorobutane, 1,1,1,3-tetrachlorobutane and 1,1,3,3-tetrachlorobutane;
 molecules of the type such as chlorobutenes, dichlorobutenes, tetrachlorobutenes and in particular trichlorobutenes such as 1,2,4-trichlorobut-2-ene, 1,3-dichloro-2-chloromethylpropene, 1,1,3-trichlorobut-1-ene, 4,4,4-trichlorobut-1-ene, 1,2,3-trichloro-1-butene, 3,4,4-trichloro-1-butene, 2-chloromethyl-3,3-dichloropropene, 1,1,4-trichlorobut-2-ene, 3,3,4-trichlorobut-1-ene, 1,1,3-trichlorobut-2-ene, 1,3,3-trichlorobut-1-ene, 1,1,2-trichlorobut-1-ene, 1,1,1-trichlorobut-2-ene, 1,1,4-trichlorobut-2-ene, 1,3,4-trichlorobut-1-ene, 1,1,2-trichlorobut-2-ene, 1,2,3-trichlorobut-2-ene, 2-methyl-1,1,3-trichloro-1-propene, 1,2,4-trichlorobut-2-ene, 2,3,4-trichlorobut-1-ene.

Thus, advantageous compositions according to the invention:
 comprise at least one compound from among the chlorobutane series in a content of less than or equal to 0.5%; or less than or equal to 1000 ppm; or less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and, for example, from 1 to 5 ppm; or alternatively
 comprise a compound from among the chlorobutene series, the total content of all these compounds being less than or equal to 0.5%; or less than or equal to 1000 ppm; or less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and, for example, from 1 to 5 ppm; or alternatively
 comprise at least one compound from among the chlorobutanes and chlorobutenes, in a content of less than or equal to 0.5%; or less than or equal to 1000 ppm; or less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and, for example, from 1 to 5 ppm.

Other particularly undesirable impurities mixed in the reaction medium are also molecules containing an oxygen heteroatom such as acids, esters, aldehydes or oxychlorides, especially phosgene. This compound is particularly known for its toxicity. In the presence of hydrogen fluoride, these oxygenated compounds are liable to decompose to form water. Water is an element whose content must be minimized since it can accentuate corrosion phenomena in HF medium.

Thus, advantageous compositions according to the invention:

comprise at least one oxygenated compound, in a content of less than or equal to 0.5%; or less than or equal to 1000 ppm; or less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and, for example, from 1 to 5 ppm.

Preparation of the Compositions According to the Invention

The compositions of the invention may be efficiently obtained from carbon tetrachloride via F-240fa, by:

reaction of carbon tetrachloride with vinyl chloride to produce F-240fa;

dehydrochlorination of F-240fa to obtain F-1230za.

Alternatively, the process for preparing the compositions comprises the following steps:

reaction of carbon tetrachloride with ethylene to produce F-250fb;

chlorination reaction of F-250fb (1,1,1,3-tetrachloropropane) to manufacture predominantly F-240fa;

dehydrochlorination of F-240fa to obtain F-1230za.

The compositions according to the invention may then be obtained by performing one or more steps for separating F-1230za from the other compounds mentioned above, and especially from F-240fa (which is generally the major side product of the dehydrochlorination) and also other telomerization/dehydrochlorination side products such as F-240db and/or F-1230xa.

These separation steps may preferably be performed by absorption/washing and distillation. As an alternative to distillation or in combination therewith, it is also possible to envisage separation by extractive distillation, physicochemical separations on molecular sieves, alumina or active charcoal or membrane separation.

A first separation is generally performed using standard distillation (plate column, packing column) at atmospheric pressure or under reduced pressure. The chosen pressure is less than 760 mmHg, preferentially less than 450 mmHg and more preferentially less than 200 mmHg. Inherently, the column pressure determines the temperature conditions for a chosen degree of separation. F-1230za may be recovered by performing the distillation at a temperature below 180° C., preferentially below 160° C. and more preferentially below 130° C. A single column or a distillation train may be used. Under chosen conditions, the purity of the F-1230za after distillation reaches a minimum of 99.3%.

A second separation may be performed using adsorption on zeolite or active charcoal.

The zeolites or active charcoals that may be used in the process for purifying F-1230za advantageously have a mean pore size of from 3.4 to 11 Å, preferably from 3.4 to 10 Å and even more advantageously between 4 and 9 Å.

If the zeolite or active charcoal has a mean pore size of greater than 11 Å, the amount of F-1230za adsorbed increases, whereas if the mean pore size is less than 3.4 Å, the adsorption capacity of the zeolite or active charcoal is reduced.

The zeolite preferably has an Si/Al ratio of 2 or less. If the Si/Al ratio of the zeolite is greater than 2, certain impurities are liable to be not selectively adsorbed. The zeolite is preferably at least one element chosen from the group consisting of 4 A molecular sieves, 5 A molecular sieves, 10x molecular sieves and 13x molecular sieves.

The zeolite and the active charcoal are preferably used individually for the purpose of regenerating the adsorbent, but they may also be used as a mixture. The proportions of zeolite and of active charcoal in the mixture are not particularly large.

To treat F-1230za with zeolite and/or active charcoal in the liquid phase, use may be made of a batch process or a continuous process. Industrially, a process consisting in continuously passing F-1230za through a fixed bed is preferable. The liquid hourly space velocity (LHSV) may be chosen appropriately as a function of the content of impurities to be removed and of the amount of F-1230za to be treated. In general, the space velocity is preferably from 1 to 50 $h^{-1}$. Industrially, the purification process may alternatively use two adsorption towers.

The treatment temperature for F-1230za is from 0° C. to 120° C., preferably from 20° C. to 80° C. If the treatment temperature is above 120° C., the cost of the equipment may increase on account of the heating of the apparatus, whereas if the treatment temperature is below 0° C. cooling equipment may be necessary. The pressure is from 0 to 3 MPa and preferably from 0 to 1 MPa. If the pressure is greater than 3 MPa, the profitability may decrease on account of the requirements in terms of pressure resistance of the apparatus.

A membrane separation technique may also be used in addition to adsorption on active charcoal or on zeolite, or else as an alternative to these techniques. Membrane separation may be performed in the gas phase via a continuous process implemented at low pressure, or at reduced pressure.

The chosen pressure is less than 5 bar, preferentially less than 2 bar and more preferentially less than atmospheric pressure. The choice of the membrane depends on the properties of the impurities to be separated from the F-1230za (difference in solubility, diffusivity and permeability). The membrane separation is performed at a temperature that depends on the chosen pressure, below 250° C., preferentially below 230° C. and more preferentially below 180° C.

According to a preferred embodiment, several separation techniques are combined, such as distillation or extractive distillation followed by separation by adsorption onto molecular sieves. The zeolites that may be used in the process for purifying F-1230za advantageously have a mean pore size of from 3.4 to 11 Å, preferably from 3.4 to 10 Å and even more advantageously between 4 and 9 Å. The adsorption step is performed at a temperature of between 0 and 120° C., advantageously between 5 and 100° C. and preferably between 10 and 80° C.

When F-1230za containing impurities is placed in contact with zeolite and/or active charcoal in the liquid phase and/or is purified on a membrane in the gas phase under the conditions described above, F-1230za may be obtained in a purity of greater than 99.9%.

Manufacture of F-1233zdE

The compositions according to the invention may be used for the manufacture of F-1233zdE, F-1234zeE and/or F-245fa via one or more fluorination steps, preferably in a single step.

The fluorination is a fluorination not catalyzed with HF in the liquid phase. By adjusting the operating conditions (temperature, pressure), the formation of F-1234ze and/or F-245fa can be promoted to increase their content in the resulting stream. Increasing the content of F-1234ze may also be obtained in another embodiment by recycling the F-1233zd and F-245fa into the reactor after separation of the F-1234ze. Increasing the content of F-245fa may also be obtained in another embodiment by recycling the F-1233zd and F-1234ze into the reactor after separation of the F-245fa.

The liquid-phase fluorination reaction may be performed:
- with an HF/1,1,3,3-tetrachloropropene mole ratio preferably between 5 and 15, preferably between 6 and 15, even more preferentially between 8 and 15, advantageously between 9 and 14 and preferentially between 9 and 12. The HF/1,1,3,3-tetrachloropropene mole ratio includes the recycled portion of HF and is preferably measured at the reactor inlet.
- at a reaction temperature preferably between 80 and 120 and advantageously between 90 and 110° C.
- at a pressure of between 5 and 20 bar, preferentially between 5 and 15 bar, even more preferentially between 7 and 15 bar and advantageously between 7 and 12 bar.

The fluorination reaction is preferably performed in a non-stirred reactor.

The reactor is preferably a metallic reactor. The metal of the reactor may be steel or stainless steel. However, other materials such as a super-austenitic stainless steel or an alloy based on passivatable nickel may be used. The absence of catalyst for the reaction is an advantage which makes it possible to prevent corrosion phenomena known to those skilled in the art when a fluorination catalyst is used in this type of reactor.

A removal pipe makes it possible to purge an amount of undesirable products of high molecular weight that might have formed during the fluorination reaction. This stream also contains HF and upgradeable organic compounds which are separated out via a specific treatment before being returned into the reactor, using, for example, decantation or azeotropic distillation, and preferably a combination of the two.

The process according to the present invention for fluorinating the composition thus separated out may be performed in continuous, discontinuous or batch mode. In a preferred embodiment, the process is performed in continuous mode.

The stream of products derived from the fluorination may undergo suitable treatments (distillation, washing, etc.) so as to recover the F-1233zdE in purified form and to separate it from the other compounds present (HCl, unreacted HF, cis-1233zd isomer, other organic compounds). One or more streams may be subjected to recycling.

Thus, in a preferred embodiment, the invention relates to a process for manufacturing, performed by fluorination, in the liquid phase and in the absence of catalyst, F-1233zd, and/or F-1234ze and/or F-245fa, comprising the steps:
- of introducing into a fluorination reactor a stream comprising the composition of 1,1,3,3-tetrachloropropene (F-1230za), or a mixture of 1,1,3,3-tetrachloropropene and 1,3,3,3-tetrachloropropene (F-1230zd), according to the invention.

The process is especially useful for preparing trans-1-chloro-3,3,3-trifluoropropene (F-1233zdE) or trans-1,3,3,3-tetrafluoropropene (F-1234zeE).

Finally, the invention relates more generally to the use of the compositions according to the invention for manufacturing F-1233zdE in a high purity of the order of 99.9%, and comprising a reduced content of particular impurities.

A particular impurity consists of the isomer 1233xf (2-chloro-3,3,3-trifluoropropene) which may be derived from the chloro compounds 240db or 1230xa. The boiling point of this isomer is relatively close to our final compound and might lead to separation problems.

Other impurities whose boiling point is also close to that of the compound F-1233zd and containing four carbons may originate from the fluorination of chlorobutenes and/or chlorobutanes and may prove to be an interference in the process since they are difficult to separate out. These impurities are chosen from the following list:
- 1,1,1-trifluorobutane or F-383mff or $CF_3-CH_2-CH_2-CH_3$
- 1,1,1,4,4-pentafluorobutane or F-365mff or $CF_3-CH_2-CH_2-CHF_2$
- 2,2,3,3-tetrafluorobutane or F-374scc or $CH_3-CF_2-CF_2-CH_3$
- 1,1,1,2,2,4,4,4-octofluorobutane or F-338mcf or $CF_3-CF_2-CH_2-CF_3$
- 1,1,1,2,2,3,3-heptafluorobutane or F-347mcc or $CF_3-CF_2-CF_2-CH_3$
- 1,1,1,2,2,3,3,4,4-nonafluorobutane or F-329mcc or $CF_3-CF_2-CF_2-CHF_2$.

Other impurities whose boiling point is also close to that of the compound F-1233zd and containing three carbons may originate from the fluorination of chloropropenes and/or chloropropanes and may prove to be an interference in the process since they are difficult to separate out. These impurities are chosen from the following list:
- 1,2-difluoropropane or F-272ea or $CH_2F-CHF-CH_3$
- 1,1,2-trifluoropropane or F-263eb or $CHF_2-CHF-CH_3$
- 1,2,2,3-tetrafluoropropane or F-254ca or $CH_2F-CF_2-CH_2F$.

EXAMPLES

The following examples illustrate the invention without limiting it.

A first step consists in preparing the starting material. 1,1,3,3-Tetrachloropropene is obtained by dehydrochlorination of 1,1,1,3,3-pentachloropropane in the presence of anhydrous ferric chloride.

Example 1: Preparation of F-1230za by Dehydrochlorination of F-240fa 1626.5 g of 99.6% pure 1,1,1,3,3-pentachloropropane are placed in a jacketed glass reactor equipped with a reflux condenser. The reactor headspace is flushed with a stream of 4 l/h of nitrogen to render the atmosphere inert. 17 g of anhydrous ferric chloride are then introduced, followed by starting the stirring at 800 rpm. The reflux is fed by a fluid maintained at 20° C. The gas outlet of the condenser is connected to a water bubbler which allows the HCl that is evolved in the course of the dehydrochlorination reaction to be trapped. The mixture is then heated at 80° C. for 5 hours. 1338.1 g of resulting solution are emptied from the round-bottomed flask. The mixture obtained is filtered to remove the ferric chloride in suspension, purified with active charcoal and then analyzed by gas chromatography.

TABLE 1 dehydrochlorination of 240fa: composition of the mixture

| Compound (weight %) | Before reaction | After reaction |
|---|---|---|
| 1230za | 0.046 | 92.25 |
| 250fb | 0.029 | 0.024 |
| 240fa | 99.61 | 3.10 |
| $C_2Cl_6$ | 0.059 | 0.066 |
| 240db | 0.157 | 0.187 |
| Chlorobutenes + chlorobutanes | 0.083 | 0.127 |
| Chloropropenes + chloropropanes | 0.003 | 0.134 |

The chlorobutenes and chlorobutanes were able to be identified only by their empirical formula as $C_4H_6Cl_2$, $O_4H_7Cl_3$, $O_4H_2Cl_4$ or $O_4H_6Cl_4$. The chloropropenes and chloropropanes are 1230xa and other compounds identified by their empirical formula as $C_3H_3Cl_3$, or $C_3H_2Cl_4$ which are different from 250fb, 240fa or 240db.

The remainder of the above compositions is constituted of unidentified products.

Example 2: Distillation of 1230za

1230za of low purity is then subjected to standard laboratory distillation involving a 10-plate Oldershaw column, a condenser, a vacuum pump, a round-bottomed flask and receiver flasks. The distillation is performed under a vacuum of 25 mbar, and the product 1230za then has a boiling point of 53° C. The result of the distillation is illustrated in table 2.

TABLE 2 distillation of 1230za: composition of the mixture

| Compound (weight %) | Before distillation | After distillation |
|---|---|---|
| 1230za | 92.25 | 99.30 |
| 250fb | 0.024 | 0.021 |
| 240fa | 3.10 | 0.179 |
| $C_2Cl_6$ | 0.066 | 0.012 |
| 240db | 0.187 | 0.001 |
| Chlorobutenes + chlorobutanes | 0.127 | 0.133 |
| Chloropropenes + chloropropanes | 0.134 | 0.245 |

Example 3: Batch-Mode Fluorination of 1230za

The tests performed are batch tests at a regulated pressure. 100 g of 99.6% pure F-1230za and 115 g of HF, i.e. a mole ratio of 10.3, are successively introduced into the 1-liter stainless-steel autoclave, equipped with a condenser, a pressure indicator, a thermometer probe and a rupture disk. A cooling circulation is established in the condenser, the reactor is heated to about and the pressure gradually increases to reach 10 bar (nominal pressure); the temperature measured is then 85° C. in the reactor. At this pressure, opening of the regulating valve makes it possible to remove the light compounds. The organic products are washed and then trapped. After 24 hours, the system is returned to room temperature. The rest of the organic compounds and of the hydracids are removed from the reactor by degassing followed by flushing with helium. This results in 138 g of hydracids, 61 g of trapped organic compounds and 1.5 g of heavy black compounds at the bottom of the reactor. The weight percentage distribution of the organic compounds is as follows: 94.9% of E-1233zd, 3.3% of Z-1233zd, 0.8% of 245fa, 0.3% of E-1234ze, and also intermediate compounds such as 1232zd (1,3-dichloro-3,3-difluoroprop-1-ene) or 1232za (1,1-dichloro-3,3-difluoroprop-1-ene).

No trace of 1230za was found, thus illustrating total conversion of the reagent. The conversion is very high and the final yield of desired product E-1233zd close to 95%.

Comparative Example 4: Liquid-Phase Batch Fluorination of 240fa

A test is performed according to Example 3 by introducing 550 g of F-240fa and 580 g of HF, i.e. a mole ratio of 11. This results in 570 g of hydracids, 545 g of organic compounds and 6.1 g of heavy compounds. The weight percentage distribution of the organic compounds is as follows: 75.7% of F-240fa, 12.6% of F-241fa, 7.1% of E-1233zd, 0.2% of Z-1233zd, 3.9% of 245fa and 0.07% of intermediate compounds (1232, 242).

The degree of conversion of the F-240fa in non-catalyzed liquid phase is thus very low and the yield of desired product E-1233zd very low.

Comparative Example 5: Liquid-Phase Batch Fluorination of a 240db/240aa Mixture

The procedure of Example 3 is reproduced. The organic compound is a 240db/240aa mixture (88.5%/11.5%). 108 g of organic mixture and 101 g of HF are successively introduced into the autoclave, i.e. a mole ratio of 10.3. This results in 96 g of hydracids, 90 g of organic compounds and 2.2 g of heavy compounds. The weight percentage distribution of the organic compounds is as follows: 86.2% of F-240db, 11.9% of F-240aa, 1.3% of an isomer 241.

The degree of conversion of the F-240db and of the F-240aa in non-catalyzed liquid phase is thus very low and the yield of desired product E-1233zd nonexistent.

Comparative Example 6: Liquid-Phase Batch Fluorination of 1230xa

The procedure of Example 3 is reproduced. The organic compound is 1230xa. 90 g of 1230xa and 80 g of HF are successively introduced into the autoclave, i.e. a mole ratio of 8. This results in 90.5 g of hydracids and 66.3 g of organic compounds. The weight percentage distribution of the organic compounds is as follows: 1.2% of 1230xa, 8.7% of an isomer 1232 and 90% of unidentified heavy compounds.

The degree of conversion of the 1230xa in non-catalyzed liquid phase is high, but does not lead to the desired product, E-1233zd. It rapidly converts into heavy compounds that are difficult to identify.

Examples 3 to 6 show the results obtained for the non-catalyzed fluorination reaction for the following reagents: 1230za, 240fa, 240db, 240aa and 1230xa. With the exception of 1230za, all the other yields of E-1233zd are very low.

The invention claimed is:
1. A composition comprising:
    at least 99.5% by weight of 1,1,3,3-tetrachloropropene (F-1230za), or at least 99.5% by weight of a mixture comprising 1,1,3,3-tetrachloropropene and 1,3,3,3-tetrachloropropene (F-1230zd), and
    at least one additional compound selected from the group consisting of chlorobutenes and chlorobutanes, wherein the amount of said additional compound or the total amount of said compounds represents a content of less than or equal to 500 ppm, in the composition.

2. The composition as claimed in claim 1, in which said additional compound represents a content of less than or equal to 450 ppm, in the composition.

3. The composition as claimed in claim 1, in which said additional compound is selected from the group consisting of monochlorobutanes, dichlorobutanes, trichlorobutanes, and tetrachlorobutanes.

4. The composition as claimed in claim 3, in which said additional compound is selected from the group consisting of 1,1,4,4-tetrachlorobutane, 1,2,3,4-tetrachlorobutane, 1,1,1,3-tetrachlorobutane, and 1,1,3,3-tetrachlorobutane.

5. The composition as claimed in claim 1, in which said additional compound is selected from the group consisting of monochlorobutenes, dichlorobutenes, trichlorobutenes, and tetrachlorobutenes.

6. The composition as claimed in claim 5, in which said additional compound is selected from the group consisting of 1,2,4-trichlorobut-2-ene, 1,3-dichloro-2-chloromethylpropene, 1,1,3-trichlorobut-1-ene, 4,4,4-trichlorobut-1-ene, 1,2,3-trichloro-1-butene, 3,4,4-trichloro-1-butene, 2-chloromethyl-3,3-dichloropropene, 1,1,4-trichlorobut-2-ene, 3,3,4-trichlorobut-1-ene, 1,1,3-trichlorobut-2-ene, 1,3,3-trichlorobut-1-ene, 1,1,2-trichlorobut-1-ene, 1,1,1-trichlorobut-2-ene, 1,1,4-trichlorobut-2-ene, 1,3,4-trichlorobut-1-ene, 1,1,2-trichlorobut-2-ene, 1,2,3-trichlorobut-2-ene, 2-methyl-1,1,3-trichloro-1-propene, 1,2,4-trichlorobut-2-ene, and 2,3,4-trichlorobut-1-ene.

7. A process for manufacturing the composition as claimed in claim 1, comprising the following steps:
reaction of carbon tetrachloride with vinyl chloride to produce 1,1,1,3,3-pentachloropropane (F-240fa);
dehydrochlorination of F-240fa to obtain 1,1,3,3-tetrachloropropene (F-1230za);
one or more steps for separating out the F-1230za.

8. The process as claimed in claim 7, in which the separation is performed by distillation or extraction, and/or by physicochemical separation on molecular sieves, alumina or active charcoal, and/or by membrane separation, optionally in the gas phase.

9. The process as claimed in claim 8, in which a first separation step is performed via one or more distillations and a second separation step is performed by adsorption on molecular sieves, on active charcoal or on a mixture thereof.

10. The process as claimed in claim 8, in which the separation step is performed by adsorption on zeolite, and optionally followed by gas-phase membrane separation.

11. The process as claimed in claim 8, in which the step of separation by adsorption is performed at a temperature of between 0 and 120° C.

12. A process for manufacturing the composition as claimed in claim 1, comprising the following steps:
reaction of carbon tetrachloride with ethylene to produce 1,1,1,3-tetrachloropropane (F-250fb);
chlorination of F-250fb to obtain 1,1,1,3,3-pentachloropropane (F-240fa);
dehydrochlorination of F-240fa to obtain 1,1,3,3-tetrachloropropene (F-1230za);
one or more steps for separating out the F-1230za.

13. A process for manufacturing 1-chloro-3,3,3-trifluoropropene (F-1233zd), and/or 1,3,3,3-tetrafluoropropene (F-1234ze) and/or 1,1,1,3,3-pentafluoropropane (F-245fa), by fluorination performed in the liquid phase and in the absence of catalyst, comprising the steps:
introducing into a fluorination reactor a stream comprising the composition as claimed in claim 1.

14. The process as claimed in claim 13 for forming trans-1-chloro-3,3,3-trifluoropropene (F-1233zdE) or trans-1,3,3,3-tetrafluoropropene (F-1234zeE).

15. The process as claimed in claim 13, followed by one or more steps for separating 1-chloro-3,3,3-trifluoropropene (F-1233zd), and/or 1,3,3,3-tetrafluoropropene (F-1234ze) and/or 1,1,1,3,3-pentafluoropropane (F-245fa) from the stream of products.

* * * * *